(12) United States Patent
Venugopala et al.

(10) Patent No.: US 11,530,217 B1
(45) Date of Patent: Dec. 20, 2022

(54) ANTITUBERCULAR COMPOUNDS

(71) Applicant: KING FAISAL UNIVERSITY, Hofouf (SA)

(72) Inventors: Katharigatta N. Venugopala, Hofouf (SA); Mahesh Attimarad, Hofouf (SA); Anroop B. Nair, Hofouf (SA); Nagaraja Sreeharsha, Hofouf (SA); Mohamed A. Morsy, Hofouf (SA); Sandeep Chandrashekharappa, Hofouf (SA); Melendran Pillay, Hofouf (SA); Pran Kishore Deb, Hofouf (SA)

(73) Assignee: KING FAISAL UNIVERSITY, Hofouf (SA)

( * ) Notice: Subject to any disclaimer, the term of this patent is extended or adjusted under 35 U.S.C. 154(b) by 0 days.

(21) Appl. No.: 17/853,618

(22) Filed: Jun. 29, 2022

(51) Int. Cl.
*C07D 471/04* (2006.01)
*A61P 31/06* (2006.01)

(52) U.S. Cl.
CPC ............ *C07D 471/04* (2013.01); *A61P 31/06* (2018.01)

(58) Field of Classification Search
CPC ................................ C07D 471/04; A61P 31/06
USPC ........................................................ 514/227.8
See application file for complete search history.

(56) References Cited

U.S. PATENT DOCUMENTS

| 10,435,402 | B2 | 10/2019 | Mukhopadhyay et al. |
| 2003/0204090 | A1 | 10/2003 | Ono et al. |
| 2009/0143449 | A1 | 6/2009 | Bonnert et al. |
| 2010/0048638 | A1* | 2/2010 | Crawford ............ A61K 31/5377 514/341 |
| 2016/0113919 | A1 | 4/2016 | Banaei et al. |

FOREIGN PATENT DOCUMENTS

| CN | 110183444 | A | 8/2019 |
| CN | 111875601 | A | 11/2020 |
| CN | 113563328 | A | 10/2021 |

OTHER PUBLICATIONS

Venugopala et al., "Computational, crystallographic studies, cytotoxicity and anti-tubercular activity of substituted 7-methoxy-indolizine analogues," PLOS ONE, 14(6), 2019.
Venugopala et al., "Anti-Tubercular Activity of Substituted 7-Methyl and 7-Formylindolizines and In Silico Study for Prospective Molecular Target Identification," Antibiotics, 8, 2473, Dec. 2019.
Venugopala et al., "Anti-tubercular activity and molecular docking studies of indolizine derivatives targeting mycobacterial InhA enzyme," J Enzyme Inhib Med Chem., Dec. 2021; 36(1):1472-1487, Published online: Jul. 1, 2021.

* cited by examiner

*Primary Examiner* — Niloofar Rahmani
(74) *Attorney, Agent, or Firm* — Nath, Goldberg & Meyer; Richard C. Litman

(57) ABSTRACT

Anti-tubercular compounds include trisubstituted indolizines having the following structural formula:

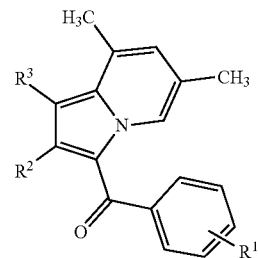

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

11 Claims, 1 Drawing Sheet

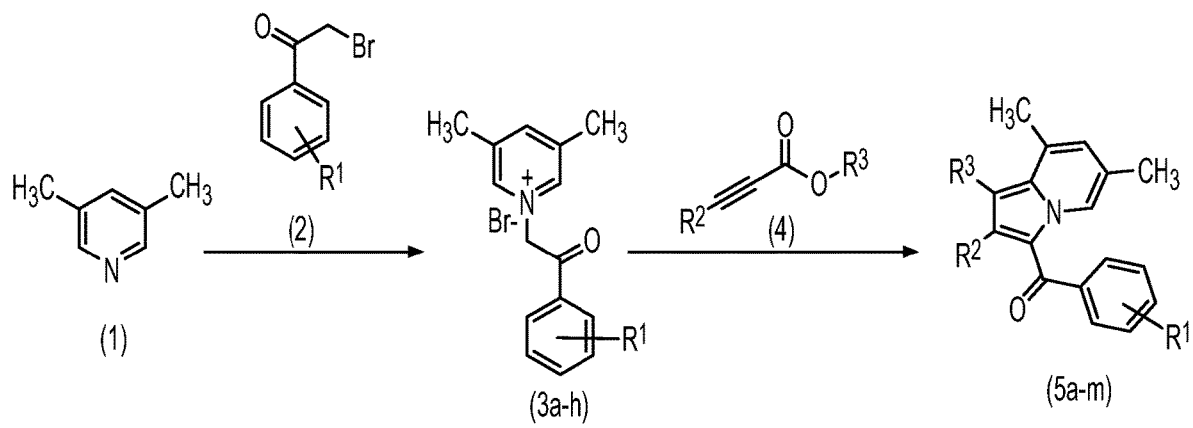
| COMPOUND NO. | R¹ |
|---|---|
| 3a | 4-OCH₃ |
| 3b | 4-Cl |
| 3c | 4-Br |
| 3d | 4-F |
| 3e | 2-NO₂ |
| 3f | 3,5-CF₃ |
| 3g | CN |
| 3h | CH₃ |
| COMPOUND NO. | R¹ | R² | R³ |
|---|---|---|---|
| 5a | 4-OCH₃ | COOC₂H₅ | H |
| 5b | 4-OCH₃ | COOCH₃ | COOCH₃ |
| 5c | 4-Cl | COOC₂H₅ | H |
| 5d | 4-Cl | COOCH₃ | COOCH₃ |
| 5e | 4-Br | COOC₂H₅ | H |
| 5f | 4-Br | COOCH₃ | COOCH₃ |
| 5g | 4-F | COOC₂H₅ | H |
| 5h | 2-NO₂ | COOC₂H₅ | H |
| 5i | 3,5-CF₃ | COOC₂H₅ | H |
| 5j | 4-CN | COOC₂H₅ | H |
| 5k | 4-CH₃ | COOC₂H₅ | H |
| 5l | 4-CN | COOCH₃ | COOCH₃ |
| 5m | 4-CH₃ | COOCH₃ | COOCH₃ |

ANTITUBERCULAR COMPOUNDS

BACKGROUND

1. Field

The disclosure of the present patent application relates to compounds for treating tuberculosis and, particularly, to anti-tubercular compounds that are 1,2,3,6,8-pentasubstituted indolizines and their use as anti-tubercular agents.

2. Description of the Related Art

Tuberculosis (TB) is a communicable infectious disease and a major cause of illness, particularly in low-income countries. It is caused by the opportunistic *bacillus Mycobacterium tuberculosis* (MTB), which primarily attacks the lungs (pulmonary), but may later affect other parts (extrapulmonary) of the body. Several factors have contributed to the continuous health threat of TB globally, including the development of drug resistance, such as multidrug-resistant tuberculosis (MDR-TB), extensively drug-resistant tuberculosis (XDR-TB), and totally drug-resistant tuberculosis (TDR-TB); the co-morbidities with acquired immunodeficiency syndrome (AIDS), and the risks involved in developing diabetes mellitus among TB patients.

New therapeutic strategies are needed to combat the tuberculosis pandemic and the growing resistance to conventional anti-TB drugs, which remain a serious public health challenge worldwide. Bedaquiline, Delamanid, and Pretomanid are anti-tubercular drugs that have been widely used during the past couple of years to treat tuberculosis. As these drugs are typically not effective by themselves, they are usually combined with first-line and second-line anti-TB drugs. These conventional anti-TB drugs are associated with significant side effects. Further, clinical resistance to conventional anti-TB drugs has been widely reported in extensively drug-resistant tuberculosis (XDR-TB) patients.

A promising emerging approach to overcome MDR-TB is the development of multi-targeting compounds in which a single molecule has the ability to bind to different biological targets. This concept is known as poly-pharmacology and has proven promising in terms of efficacy, synergistic effect, adverse events, and in preventing both drug-drug interaction and resistance insurgence. For instance, SQ109, a drug candidate in the TB drug development pipeline, exhibits its anti-TB activity by acting on multiple targets. SQ109 is a well-known MmpL3 inhibitor that also shows inhibitory activity against MenA and MenG MTB enzymes as well. In addition, several natural products have also been reported as lead molecules against clinical MDR strains of MTB. Therefore, the discovery of novel chemical entities having multiple modes of action is of paramount importance in the treatment of MDR, XDR, and TDR-TB infections.

Indolizine represents a privileged scaffold for the development of bioactive compounds. Several synthetic indolizines have been reported to possess a broad spectrum of pharmacological activities, such as analgesic, anti-inflammatory, anticancer, antidiabetic, antihistaminic, COX-2 inhibition, antileishmanic, antimicrobial, antimutagenic, antioxidant, antiviral, larvicidal, herbicidal and α7 nAChR inhibitors, anti-alzheimer, antischizophrenic, anticonvulsant and inhibitors of various enzymes.

Thus, anti-tubercular compounds solving the aforementioned problems are desired.

SUMMARY

Anti-tubercular compounds include 1,2,3,6,8-pentasubstituted indolizines having the following structural formula:

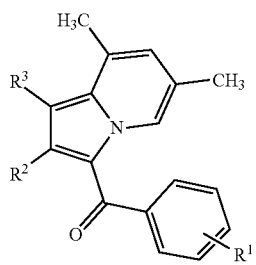

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

Specifically, the anti-tubercular compounds can include one or more of the following compounds:

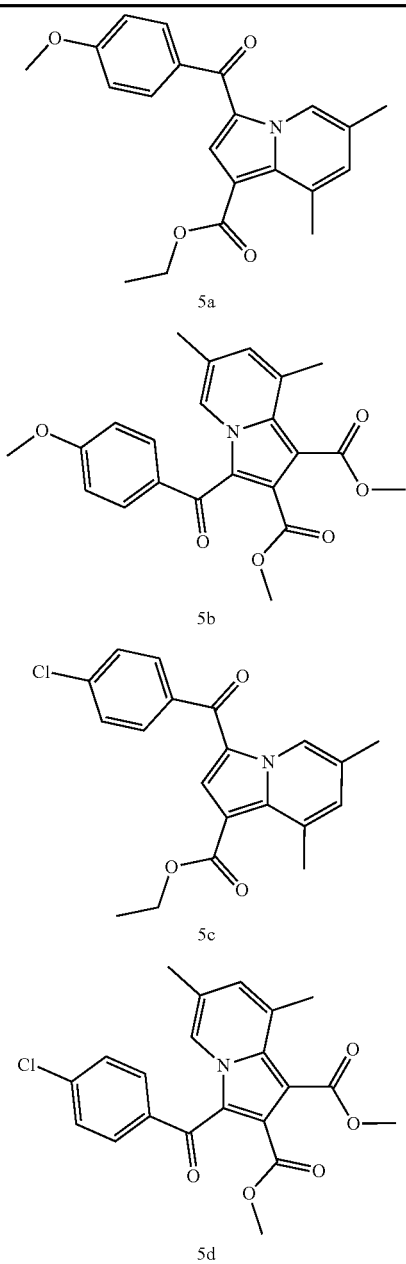

5a

5b

5c

5d

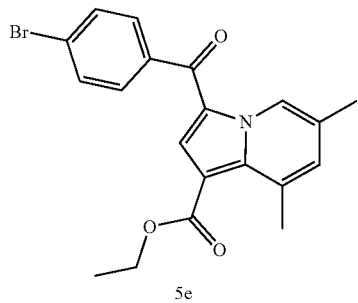

5e

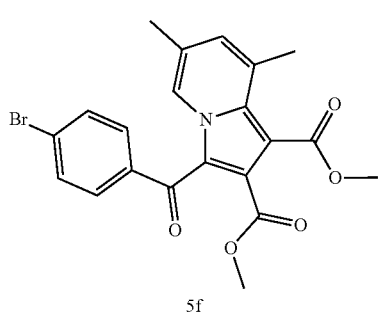

5f

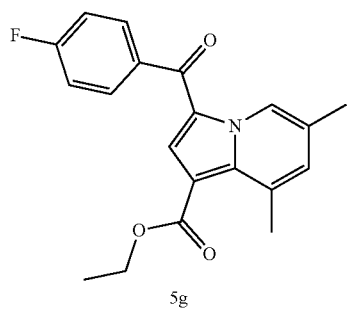

5g

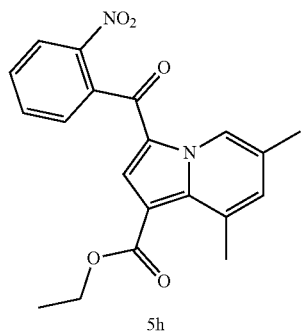

5h

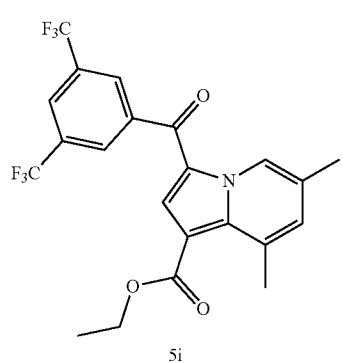

5i

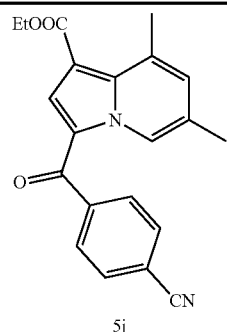

5j

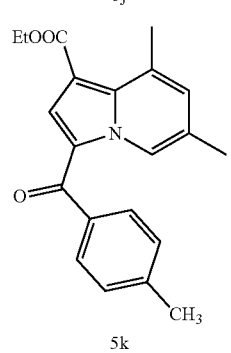

5k

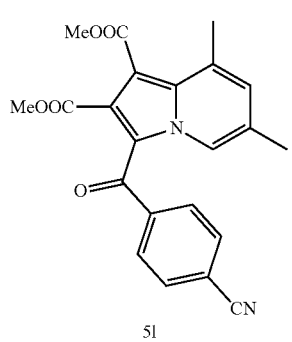

5l

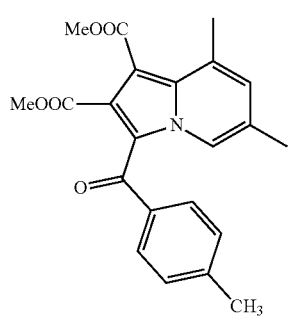 [SMILES: COC(=O)c1c(C(=O)OC)c2c(C)cc(C)cn2c1C(=O)c1ccc(C)cc1]

5m

The anti-tubercular compounds exhibit anti-TB activity against H37Rv, and multiple drug resistance (MDR) strains of *Mycobacterium tuberculosis*. The compounds exhibit anti-TB properties at millimolar to micromolar concentrations when tested alone against whole-cell *Mycobacterium tuberculosis* organisms. Accordingly, the anti-tubercular compounds can be effective agents for treating a patient suffering from tuberculosis.

These and other features of the present subject matter will become readily apparent upon further review of the following specification.

BRIEF DESCRIPTION OF THE DRAWINGS

FIG. 1 is an exemplary reaction scheme for synthesis of 1,2,3,6,8-pentasubstituted indolizine derivatives 5a-5m.

Similar reference characters denote corresponding features consistently throughout the attached drawings.

DETAILED DESCRIPTION OF THE PREFERRED EMBODIMENTS

Anti-tubercular compounds include indolizine derivatives having the following structural formula:

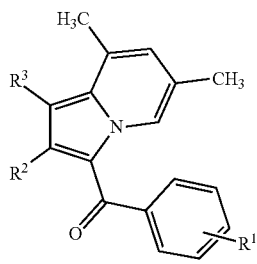

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

Specifically, the anti-tubercular compounds can include one or more of the following compounds:

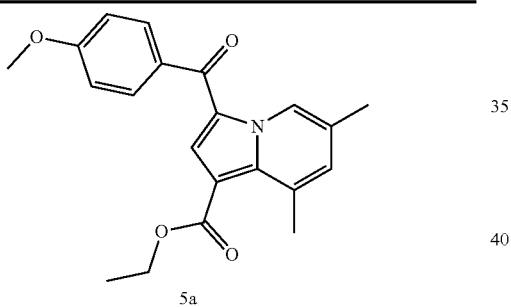

5a

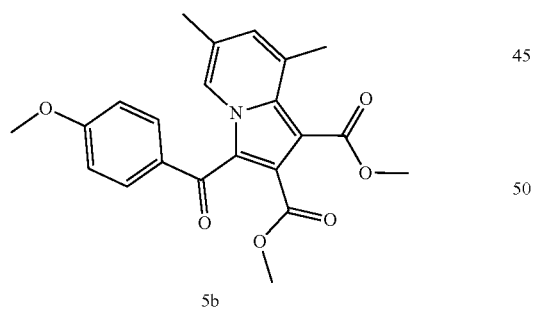

5b

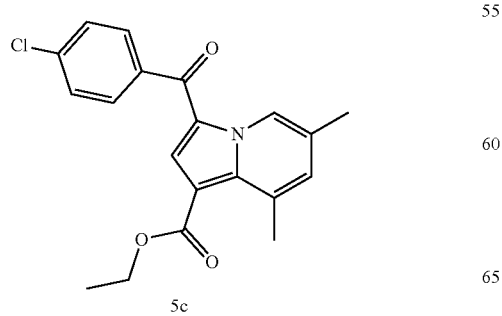

5c

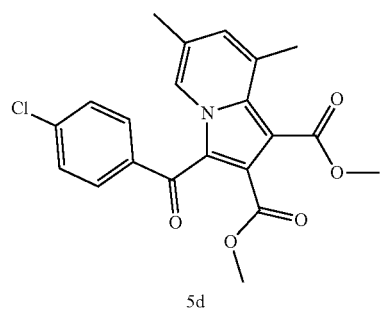

5d

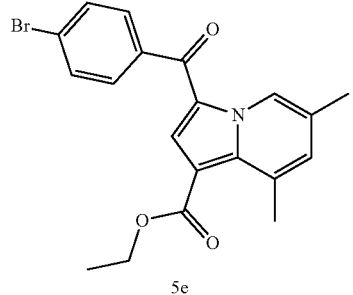

5e

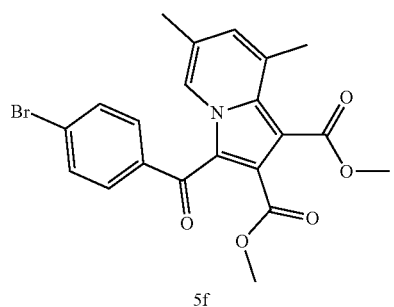

5f

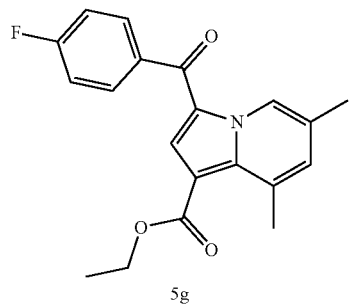

5g

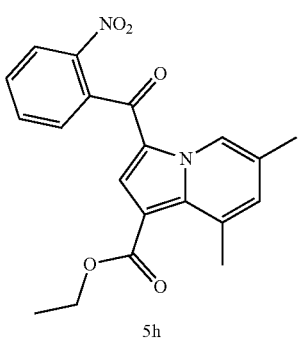

5h

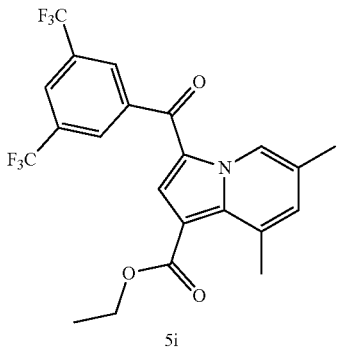

5i

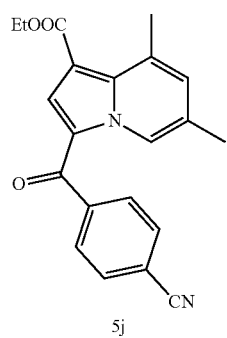

5j

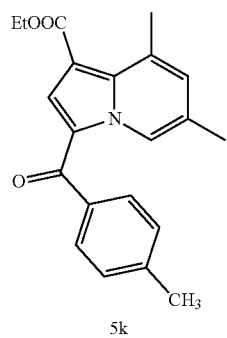

5k

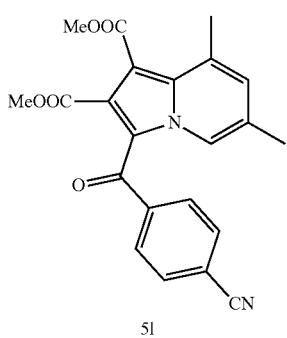

5l

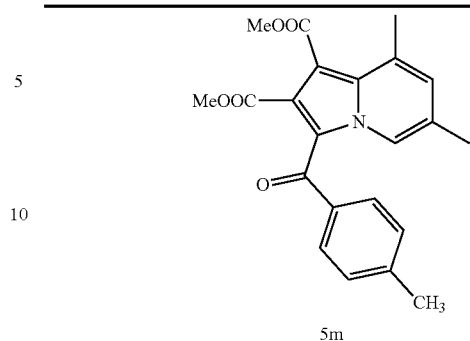

5m

The anti-tubercular compounds exhibit anti-TB activity against H37Rv and multiple drug resistance (MDR) strains of *Mycobacterium tuberculosis*. It is believed that the mycobacterial enyol-ACP-reductase (InhA) enzyme is the principal drug target of the compounds. The compounds exhibit anti-TB properties at millimolar to micromolar concentrations against whole cell *Mycobacterium tuberculosis* organisms. Accordingly, the anti-tubercular compounds can be effective agents for treating tuberculosis.

The present compounds were obtained by structural modifications of the indolizine scaffold which has previously demonstrated potential antimycobacterial activity. As described in detail herein, a series of 1,2,3,6,8-pentasubstituted indolizine derivatives (5a-5m) were evaluated for their anti-TB activity against susceptible and MDR-MTB strains. A majority of the tested compounds demonstrated good to excellent anti-tubercular activity with MIC ranging from 4 µg/mL to 64 µg/mL. The inhibition profile of indolizines and molecular docking provide strong indication that InhA is the principal drug target for the investigated compounds. Molecular modelling insight indicated that the conformation changes resulting from the benzoyl group rotation provided a rationale for the MTB cellular activity of the indolizines as InhA inhibitor. Furthermore, the cellular activity profile of the ester indolizine derivatives (5a-5m) against both the strains revealed their inhibitory action in multiple molecular targets in which anthranilate phosphoribosyltransferase might be a potential additional drug target. The results highlighted the importance of indolizines as a novel promising class of multi-targeting agents for MTB with favorable toxicity profile.

A pharmaceutical composition for treating tuberculosis can include the anti-tubercular compounds and a pharmaceutically acceptable carrier. Pharmaceutical compositions comprising one or more of the anti-tubercular compounds and a pharmaceutically acceptable carrier may be made using any technique generally known in the art. As a non-limiting example, a method of making a pharmaceutical composition includes mixing one or more of the anti-tubercular compounds with a pharmaceutically acceptable carrier. For example, the method of making a pharmaceutical composition can include mixing the anti-tubercular compounds under sterile conditions with a pharmaceutically acceptable carrier with preservatives, buffers, and/or propellants to create the pharmaceutical composition.

An embodiment of the present subject matter is directed to a method of treating tuberculosis, comprising administering to a subject in need thereof a therapeutically effective amount of the pharmaceutical composition according to the present subject matter. A therapeutically effective amount of the pharmaceutical composition or an amount effective to treat a disease, such as tuberculosis, may be determined initially from the Examples described herein and adjusted for specific targeted diseases using routine methods.

The anti-tubercular compounds or pharmaceutical compositions thereof can be administered to a subject by any suitable route. For example, the compositions can be administered nasally, rectally, intracisternally, intraperitoneally, transdermally (as by powders, ointments, or drops), and/or parenterally.

The following examples illustrate the present teachings.

The chemicals reported herein were obtained from Sigma-Aldrich Co. (St. Louis, Mo., USA), while the solvents were obtained from Millipore Sigma (Burlington, Mass., USA). Thin-layer chromatography (TLC) using silica gel (Sigma-Aldrich Co.) on aluminum foil was employed to observe the chemical reactions. N-hexane and ethyl acetate (4:6) were used as solvents. The reactions were visualized under an ultraviolet (UV)-light/iodine chamber. B-545 was used to measure the melting points (B€uchi, Labortechnik, Flawil, Switzerland). Fourier transform infrared (FT-IR) spectra were recorded on a Shimadzu FT-IR spectrophotometer. Furthermore, $^1$H- and $^{13}$C-NMR spectra were recorded on Bruker AVANCE III 400 MHz instruments using DMSO-d6 as a solvent. Chemical shifts (d) were recorded in parts per million (ppm) downfield from tetramethylsilane, while the coupling constants (J) were recorded in Hz. The splitting pattern was documented as follows: s, singlet; d, doublet; q, quartette; m, multiplet. Liquid chromatography-mass spectrometry (LC-MS; Agilent 1100 series) was used to measure the mass spectra in conjunction with the MSD, as well as 0.1% aqueous trifluoroacetic acid in an acetonitrile system on the C18-BDS column. Then, elemental analysis was carried out using the analyser FLASH EA 1112 CHN (Thermo Finnigan LLC, New York, N.Y., USA). A single-crystal X-ray diffraction study was performed using a Bruker KAPPA APEX II DUO diffractometer equipped with a CCD detector; monochromated Mo Ka radiation (k¼0.71073 Å) was used. Data collection was carried out at 173(2) K using an Oxford Cryostream cooling system featuring the Bruker Apex II software.

Example 1

Preparation of 3,5-dimethyl-1-(2-oxo-2-substituted phenylethyl)pyridin-1-ium (3a-3h) and methyl 3-substituted benzoyl-1-ethyl-6,8-dimethylindolizine-2-carboxylate (5a-5m)

Compounds 3a-3h and 5a-5m were synthesized, purified by column chromatography, and well characterized by FT-IR, NMR, LC-MS, and elemental analysis. The purity of the compounds was 99% as measured by HPLC.

The synthesis of the title compounds (5a-5m) is portrayed in the schematic provided in FIG. 1. The intermediates (3a-3h) were obtained by stirring a mixture of 3,5-dimethylpyridine, and para-substituted phenacyl bromides in a dry acetone medium at 5 h. Compounds 3a-3h on further reaction with diethyl 2-butynedioate/1-ethyl 4-methyl but-2-ynedioate in the presence of water with continuous stirring at 80° C. for 3 h resulted in the formation of title compounds 5a-5m. The resulting title compounds were purified using ethyl acetate and hexane as an eluent by column chromatography, and compound purity was found to be more than 99% with a satisfactory yield (69% to 83%). The chemical structures of the newly synthesized compounds 5a-5m were ascertained with the help of spectroscopic techniques, such as FT-IR, NMR ($^1$H and $^{13}$C), LC-MS, and elemental analysis. In LC-MS, the molecular ion peaks of these compounds 5a-5m were in good agreement with their proposed molecular masses. Elemental analysis results of the title compounds 5a-5m were within ±0.4% of the calculated values.

The primary goal of the study was to investigate the impact of the substitution pattern, in terms of nature and position of substituents, at positions 1,2,3,6, and 8 of the indolizine ring system on the anti-tubercular activity of the resultant analogues. The synthetic strategy for the development of the target compounds involved a 1.3-dipolar [3+2] cycloaddition as a key step, allowing the introduction of the substituent in the diverse position of the indolizine ring. The 1.3-dipolar [3+2] cycloaddition of pyridinium ylides with electron-deficient alkynes offered a convenient approach for the construction of an indolizine scaffold.

Example 2

General Procedure for the Preparation of methyl 3-substituted benzoyl-1-ethyl-6,8-dimethylindolizine-2-carboxylate (5a-5m)

To a stirred solution of 1-(2-(4-methoxy/chloro/bromo/fluoro/2-nitro/3,5-trifluoromethyl/4-nitrile/methyl-phenyl)-2-oxoethyl) pyridin-1-ium bromide (3a/3b/3c/3d/3e/3f/3g/3h) (0.0016 mol), in water (10 mL), was added substituted diethyl 2-butynedioate/1-ethyl 4-methyl but-2-ynedioate (0.0016 mol), stirred at 80° C. for 3 h. Completion of the reaction was monitored by TLC. The reaction mixture was diluted with ethyl acetate. The organic layer was separated, washed with brine, and dried under sodium sulfate. The crude compound was purified by recrystallization method using hexane and ethyl acetate to afford 73-89% yield of dimethyl 3-(substitutedbenzoyl)-6,8-dimethylindolizine-1,2-dicarboxylate (5a-5m). The characterization details of title compounds 5a-5m are reported below.

Ethyl 3-(4-methoxybenzoyl)-6,8-dimethylindolizine-1-carboxylate (5a). $^1$H NMR (400 MHz, CDCl$_3$) δ 9.71 (s, 1H), 7.85 (d, J=8.1 Hz, 2H), 7.78 (s, 1H), 7.29 (s, 1H), 7.13-6.98 (m, 3H), 4.33 (q, J=7.1 Hz, 2H), 3.93 (s, 3H), 2.80 (s, 3H), 2.39 (s, 3H), 1.38 (t, J=7.1 Hz, 3H); $^{13}$C NMR (100 MHz, CDCl$_3$) δ 184.29, 162.39 131.75, 131.24, 130.11, 129.07, 125.00, 124.68, 121.70, 113.68, 60.26, 55.48, 21.84, 18.26, 14.47.

Dimethyl 3-(4-methoxybenzoyl)-6,8-dimethylindolizine-1,2-dicarboxylate (5b). $^1$H NMR (400 MHz, CDCl$_3$) δ 8.90 (s, 1H), 7.73 (d, J=8.1 Hz, 2H), 7.29 (s, 1H), 7.29 (s, 1H), 6.95-6.92 (m, 2H), 3.88 (s, 3H), 3.87 (s, 3H), 3.33 (s, 3H), 2.58 (s, 3H), 2.32 (s, 3H); $^{13}$C NMR (100 MHz, CDCl$_3$) δ 185.85, 165.31, 165.06, 163.01, 133.71, 133.01, 131.13, 129.76, 128.76, 127.49, 124.88, 122.90, 120.70, 113.55, 107.28, 55.50, 52.24, 52.01, 20.18, 18.36, 18.30.

Ethyl 3-(4-chlorobenzoyl)-6,8-dimethylindolizine-1-carboxylate (5c). $^1$H NMR (400 MHz, CDCl$_3$) δ 9.76 (s, 1H), 7.77 (d, J=8.1 Hz, 2H), 7.73 (s, 1H), 7.51 (d, J=8.0 Hz, 2H), 7.12 (s, 1H), 4.36-4.31 (q, J=7.1 Hz, 2H), 2.80 (s, 3H), 2.41 (s, 3H), 1.40-1.36 (t, J=7.1 Hz, 3H); $^{13}$C NMR (100 MHz, CDCl$_3$) δ 183.72, 163.99, 138.67, 137.80, 137.54, 132.33, 131.35, 130.58, 130.39, 129.23, 128.63, 125.23, 125.15, 121.24, 108.22, 60.39, 21.79, 18.27, 14.46.

Dimethyl 3-(4-chlorobenzoyl)-6,8-dimethylindolizine-1,2-dicarboxylate (5d). $^1$H NMR (400 MHz, CDCl$_3$) δ 9.21 (s, 1H), 7.66 (d, J=7.8 Hz, 2H), 7.44 (d, J=7.6 Hz, 2H), 7.01 (s, 1H), 3.87 (s, 3H), 3.32 (s, 3H), 2.60 (s, 3H), 2.36 (s, 2H); $^{13}$C NMR (100 MHz, CDCl$_3$) δ 185.39, 164.94, 164.89, 145.16, 138.86, 138.22, 134.28, 131.36, 130.73, 130.09, 128.91, 128.65, 128.50, 125.64, 123.37, 119.76, 107.94, 52.30, 52.07, 20.24, 18.41, 18.30.

Ethyl 3-(4-bromobenzoyl)-6,8-dimethylindolizine-1-carboxylate (5e). $^1$H NMR (400 MHz, CDCl$_3$) δ 9.76 (s, 1H), 7.69 (dd, J=17.0, 7.5 Hz, 5H), 7.12 (s, 1H), 4.36-4.31 (q, J=7.1 Hz, 2H), 2.81 (s, 3H), 2.41 (s, 3H), 1.40-1.37 (t, J=7.1 Hz, 3H); $^{13}$C NMR (100 MHz, CDCl$_3$) δ 183.79, 163.97, 139.13, 137.81, 132.35, 131.59, 130.58, 130.55, 129.24, 125.99, 125.25, 125.15, 121.20, 108.26, 60.39, 21.79, 18.27, 14.46.

Dimethyl 3-(4-bromobenzoyl)-6,8-dimethylindolizine-1,2-dicarboxylate (5f). $^1$H NMR (400 MHz, CDCl$_3$) δ 9.13 (s, 1H), 7.50 (m, 4H), 6.92 (s, 1H), 3.78 (s, 3H), 3.23 (s, 3H), 2.50 (s, 3H), 2.27 (s, 3H); $^{13}$C NMR (100 MHz, CDCl$_3$) δ 185.49, 168.35, 164.92, 164.89, 142.40, 139.30, 138.65, 134.31, 132.60, 131.67, 131.52, 131.47, 130.79, 130.21, 128.99, 128.92, 127.74, 126.72, 125.68, 123.40, 119.69, 107.97, 52.31, 52.09, 20.25, 18.62, 18.42, 18.38.

Ethyl 3-(4-fluorobenzoyl)-6,8-dimethylindolizine-1-carboxylate (5g). $^1$H NMR (400 MHz, CDCl$_3$) δ 9.75 (s, 1H), 7.84 (dd, J=8.0, 5.7 Hz, 2H), 7.73 (s, 1H), 7.22 (t, J=8.5 Hz, 2H), 7.11 (s, 1H), 4.36-4.31 (q, J=7.1 Hz, 2H), 2.80 (s, 3H), 2.41 (s, 3H), 1.40-1.36 (t, J=7.1 Hz, 3H); $^{13}$C NMR (100 MHz, CDCl$_3$) δ 183.70, 165.94, 164.04, 163.44, 137.72, 136.50, 136.47, 132.20, 131.37, 131.29, 130.51, 129.19, 125.10, 121.33, 115.54, 115.32, 108.07, 60.36, 21.80, 18.27, 14.45.

Ethyl 6,8-dimethyl-3-(2-nitrobenzoyl)indolizine-1-carboxylate (5h). $^1$H NMR (400 MHz, CDCl$_3$) δ 9.83 (s, 1H), 8.24 (d, J=8.2 Hz, 1H), 7.79 (t, J=7.5 Hz, 1H), 7.70 (t, J=7.8 Hz, 1H), 7.60 (d, J=7.5 Hz, 1H), 7.36 (s, 1H), 7.16 (s, 1H), 4.31-4.26 (q, J=7.1 Hz, 2H), 2.79 (s, 3H), 2.44 (s, 3H), 1.35-1.32 (t, J=7.1 Hz, 3H); $^{13}$C NMR (100 MHz, CDCl$_3$) δ 181.29, 163.77, 146.91, 138.00, 136.34, 133.68, 132.79, 130.32, 129.71, 129.44, 129.38, 125.77, 125.40, 124.79, 121.04, 108. 60.40, 21.80, 18.25, 14.39.

Ethyl 3-(3,5-bis(trifluoromethyl)benzoyl)-6,8-dimethylindolizine-1-carboxylate (5i). $^1$H NMR (400 MHz, CDCl$_3$) δ 9.79 (s, 1H), 8.49 (s, 1H), 8.24 (s, 1H), 8.05 (d, J=38.4 Hz, 1H), 7.68 (s, 1H), 7.24 (d, J=38.4 Hz, 1H), 4.34 (q, 3H), 2.83 (s, 3H), 2.43 (s, 3H), 1.38 (t, 3H); $^{13}$C NMR (100 MHz, CDCl$_3$) δ 181.10, 167.41, 163.63, 142.18, 138.27, 133.13, 132.06, 131.72, 130.87, 129.82, 129.54, 128.95, 125.97, 125.31, 124.50, 120.51, 109.26, 60.54, 21.73, 18.31, 14.29.

Ethyl 3-(4-cyanobenzoyl)-6,8-dimethylindolizine-1-carboxylate (5j). $^1$H NMR (400 MHz, CDCl$_3$) δ 9.80 (1H, s), 7.89 (2H, d, J=8.0 Hz), 7.84 (2H, d, J=7.9 Hz), 7.67 (1H, s), 7.17 (1H, s), 4.36-4.31 (2H, q, J=7.1 Hz), 2.81 (3H, s), 2.43 (3H, s), 1.40-1.36 (3H, t, J=7.1 Hz); $^{13}$C NMR (100 MHz, CDCl$_3$) δ 182.74, 163.79, 144.20, 138.07, 132.90, 132.24, 130.82, 129.40, 129.35, 125.75, 125.30, 120.86, 118.25, 114.61, 108.89, 60.52, 21.76, 18.29, 14.44.

Ethyl 6,8-dimethyl-3-(4-methylbenzoyl)indolizine-1-carboxylate (5k). $^1$H NMR (400 MHz, CDCl$_3$) δ 9.67 (s, 1H), 7.68 (s, 1H), 7.65-7.63 (d, J=8.1 Hz, 2H), 7.25-7.23 d, J=8.1 Hz, 2H), 6.99 (s, 1H), 4.26-4.20 (q, J=7.1 Hz, 2H), 2.81 (s, 3H), 2.34 (s, 3H), 2.26 (s, 3H). 1.30-1.26 (t, J=7.1 Hz, 3H); $^{13}$C NMR (100 MHz, CDCl$_3$) δ 185.10, 169.66, 164.17, 162.66, 143.92, 141.86, 137.57, 131.92, 130.52, 130.09, 129.19, 129.08, 129.00, 128.45, 127.21, 125.09, 124.84, 121.66, 107.74, 60.26, 36.54, 31.48, 21.82, 21.70, 21.58, 18.26, 14.46.

Dimethyl 3-(4-cyanobenzoyl)-6,8-dimethylindolizine-1,2-dicarboxylate (5l). $^1$H NMR (400 MHz, CDCl$_3$) δ 9.37 (1H, s), 7.82-7.67 (4H, m), 7.08 (1H, s), 3.87 (3H, s), 3.29 (3H, s), 2.61 (3H, s), 2.40 (3H, s); $^{13}$C NMR (100 MHz, CDCl$_3$) δ 164.68, 131.96, 131.53, 129.06, 123.74, 77.35, 77.03, 76.71, 52.38, 52.12, 20.25, 18.45.

Dimethyl 6,8-dimethyl-3-(4-methylbenzoyl)indolizine-1,2-dicarboxylate (5m). $^1$H NMR (400 MHz, CDCl$_3$) δ 9.12 (s, 1H), 7.62 (d, J=8.1 Hz, 2H), 7.29-7.24 (3, 2H), 7.29 (s, 1H), 6.95 (s, 1H), 3.87 (s, 3H), 3.26 (s, 3H), 2.58 (s, 3H), 2.43 (s, 3H), 2.34 (s, 3H); $^{13}$C NMR (100 MHz, CDCl$_3$) δ 186.72, 165.17, 165.03, 142.74, 137.77, 133.93, 130.15, 129.49, 129.16, 128.92, 128.77, 128.34, 125.12, 123.16, 120.48, 107.45, 52.23, 51.89, 21.72, 21.62, 20.23, 18.38.

Example 3

Anti-Tubercular Activity

The anti-tubercular activity of the designed compounds 5a-5m were evaluated against two types of MTB strains, namely, H37Rv and well characterized MDR strains using the colorimetric Resazurin Microplate Assay (REMA) method. A 100 mL of Middelbrook 7H9 broth was aseptically prepared and dispensed in each of the wells of a 96 well flat-bottomed microtiter plate with lids (Lasec, South Africa). Each of the test compounds was accurately weighed, dissolved in the appropriate solvent, and filter sterilized using a 0.2 micron polycarbonate filter.

Stock solutions of the test samples were aliquoted into cryovials and stored at 20° C. 100 mL of the test samples were added to each of the wells containing Middlebrook 7H9 broth supplemented with 0.1% Casitone, 0.5% glycerol, and 10% OADC (oleic acid, albumin, dextrose, and catalase). The test samples were then serially diluted two folds directly in the broth of the microtiter plate to the desired concentration ranging from 128-0.125 μg/mL. Inoculums from clinical isolates were prepared fresh from Middlebrook 7H11 agar plates by scraping and re-suspending loopful of colonies into Middlebrook 7H9 broth containing glass beads. The inoculum turbidity was adjusted to a McFarland number 1 standard and further diluted to 1:10 in M7H9 broth prior to the addition of 100 mL to each of the test samples and drug-free wells. Growth control and a sterile control were also included for each isolate. Sterile M7H9 broth was added to all perimeter walls to avoid evaporation during the incubation. The plate was covered, sealed in a plastic bag, and incubated at 37° C. After 8 days of incubation, 30 mL of 0.02% working solution of resazurin salt was inoculated into each microtiter well. The plates were then incubated overnight and read the following day. A positive reaction resulted in a color change from blue to pink owing to the reduction of resazurin to rezarufin, which confirmed MTB cell viability/growth and, hence, drug resistance. The MICs were defined as the minimum drug concentration to inhibit the growth of the organism with no color changes present in the well.

The anti-tubercular activity of the target compounds (5a-5m) was evaluated (in vitro) against two different MTB strains, namely, susceptible H37Rv MTB strain, and rifampicin and isoniazid-resistant MTB strain. Rifampicin and isoniazid were also used as positive controls. Table 1 below summarizes the results.

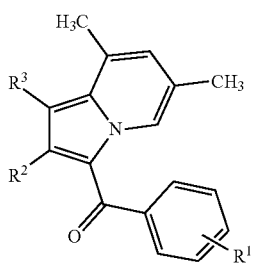

TABLE 1

In vitro anti-mycobacterial activity of
1,2,3,6,8-pentasubstituted indolizine derivatives

| Compound code | $R^1$ | $R^2$ | $R^3$ | MIC (μg/mL) H37Rv | MDR-MTB |
|---|---|---|---|---|---|
| 5a | 4-OCH$_3$ | COOC$_2$H$_5$ | H | NT | NT |
| 5b | 4-OCH$_3$ | COOCH$_3$ | COOCH$_3$ | 4 | 64 |
| 5c | 4-Cl | COOC$_2$H$_5$ | H | 0.5 | 1 |
| 5d | 4-Cl | COOCH$_3$ | COOCH$_3$ | 8 | 64 |
| 5e | 4-Br | COOC$_2$H$_5$ | H | NT | NT |
| 5f | 4-Br | COOCH$_3$ | COOCH$_3$ | NT | NT |
| 5g | 4-F | COOC$_2$H$_5$ | H | 4 | 4 |
| 5h | 2-NO$_2$ | COOC$_2$H$_5$ | H | 4 | 4 |
| 5i | 3,5-CF$_3$ | COOC$_2$H$_5$ | H | 4 | 16 |
| 5j | 4-CN | COOC$_2$H$_5$ | H | 0.5 | 4 |
| 5k | 4-CH$_3$ | COOC$_2$H$_5$ | H | 0.5 | 4 |
| 5l | 4-CN | COOCH$_3$ | COOCH$_3$ | 4 | 8 |
| 5m | 4-CH$_3$ | COOCH$_3$ | COOCH$_3$ | 0.25 | 1 |

NT = Not tested

As shown in Table 1, the antimycobacterial activity showed that compound 5m, substituted with a methyl group at the 4-position of the benzoyl group and dimethyl ester groups at the 1 and 2-position of the indolizine ring, is the most potent molecule, demonstrating the highest inhibitory action against the susceptible H37Rv MTB and MDR-MTB strains with MIC value of 0.25 μg/mL and 1 μg/mL, respectively. Compounds 5j, and 5k were found to be equipotent, with a MIC value of 0.5 μg/mL and 4 μg/mL against H37Rv MTB and MDR-MTB strains, respectively. Two compounds 5g and 5h were also found to be equipotent, with a MIC value of 4 μg/mL against both H37Rv MTB and MDR-MTB strains, respectively. Compounds 5b and 5i even though they exhibited similar activity against H37Rv MTB at 4 μg/mL but they exhibited different activity against MDR-MTB strains at 64 and 16 μg/mL, respectively. Compounds 5a, 5d, and 5f were not used for anti-TB screening.

Example 4

Safety Studies (In Vitro)

The safety of the tested indolizines was evaluated by MTT assay. The MTT (3-(4,5-dimethylthiazol-2-yl)-2,5-diphenyltetrazolium bromide) cytotoxicity assay was used to evaluate the cytotoxic effect of the most promising compounds against peripheral blood mononuclear cells (PBMCs) according to the described protocol. Cells were pipetted (90 mL of cell culture, 1_105 cells/mL) into each well of 96-well microtiter plates, and the outer wells were filled with PBS (phosphate buffer saline) in order to prevent the medium from evaporation during incubation. Thereafter, plates were incubated at 37° C. for 24 h. Each well of the plate was then treated with 10 mL of the compounds (1000-5 μg/mL). In the control wells, the negative control DMSO (dimethyl sulfoxide) and media were added. Thereafter, the plates were incubated for 2 days at 37° C. in a humidified incubator that contained a 5% CO$_2$ atmosphere. After the incubation time, 20 mL of MTT reagent (5 μg/mL) was further added to the individual well. The plate was then incubated for a further 4 h at 37° C. (5% CO$_2$ incubator). The media was then removed, and an aliquot of 100 mL DMSO was added to each well in order to dissolve the formazan crystals that were formed in metabolically active cells. After that, plates were incubated for an extra hour. The absorbance of the formazan was evaluated at 590 nm using an ELISA plate reader (Thermo Scientific Multiskan GO).

It is to be understood that the anti-tubercular compounds are not limited to the specific embodiments described above but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. Anti-tubercular compounds having the formula:

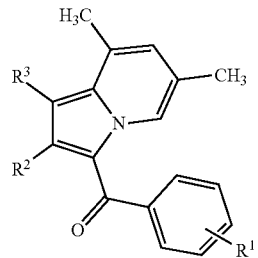

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

2. The anti-tubercular compounds of claim 1, wherein the compound is selected from the group consisting of

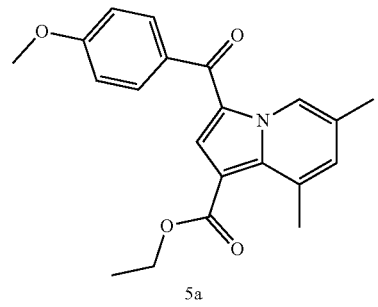

5a

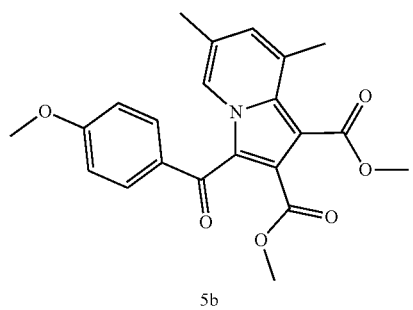

5b

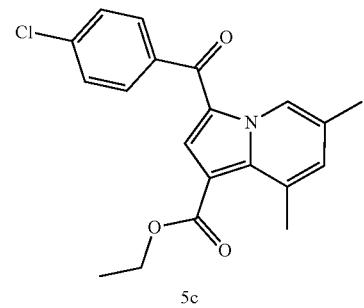
5c
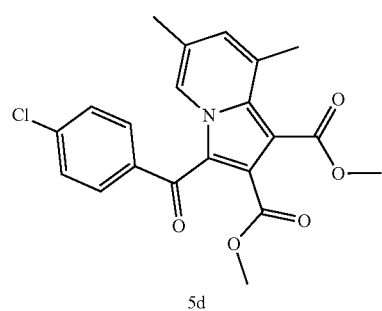
5d
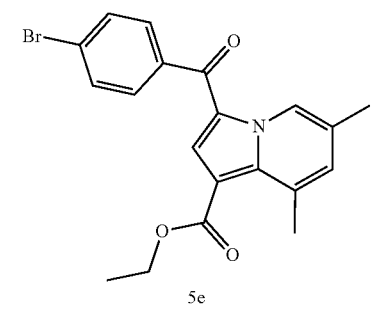
5e
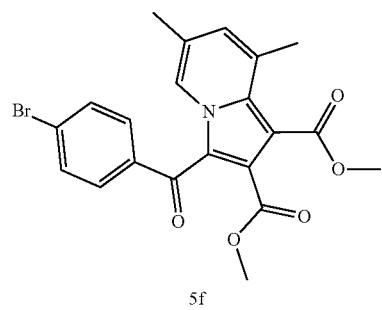
5f
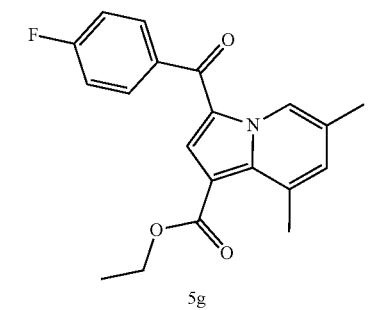
5g
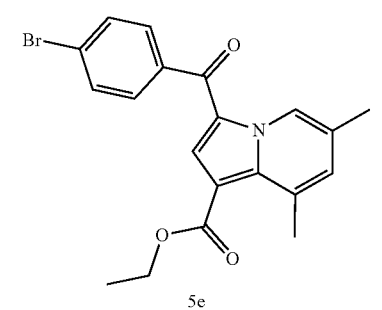
5h
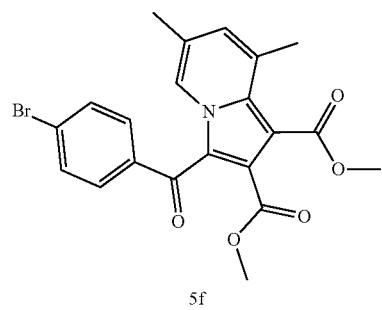
5i
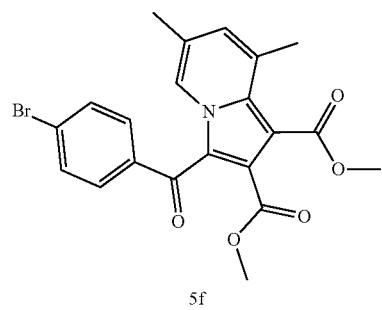
5j
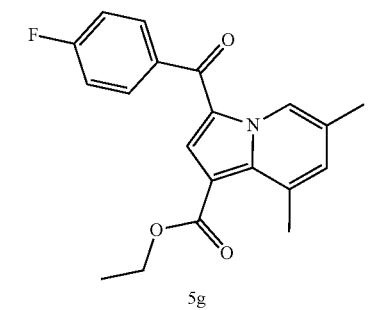
5k

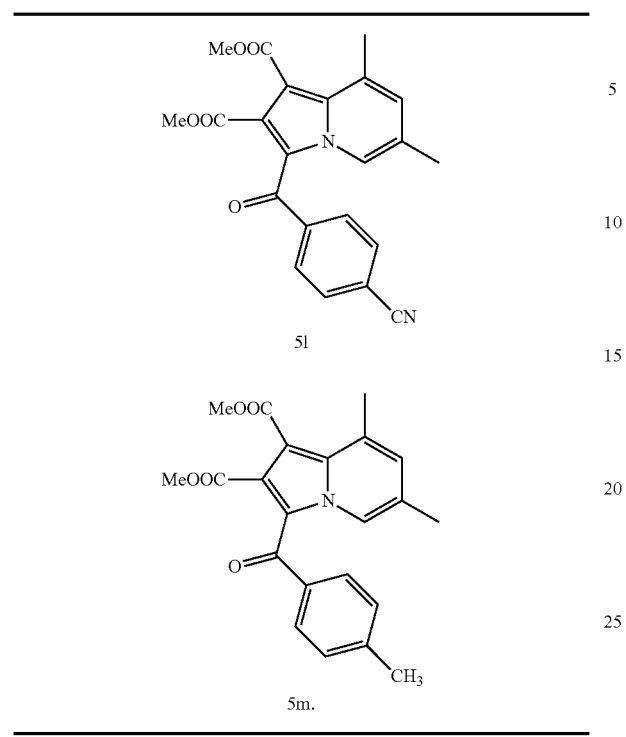

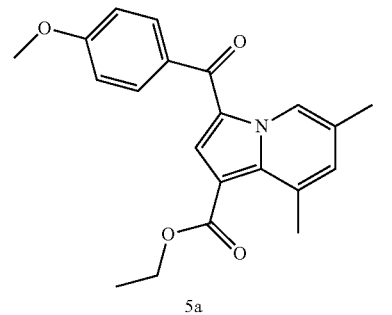

5a

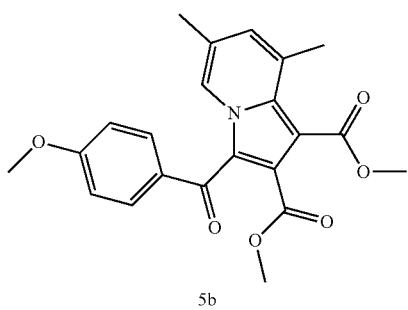

5b

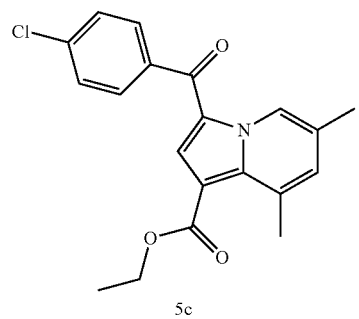

5c

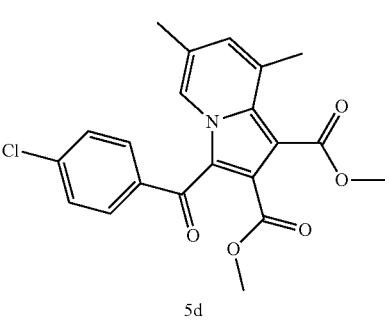

5d

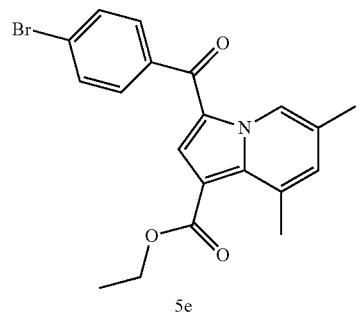

5e

3. A pharmaceutical composition, comprising the antitubercular compounds of claim 1 and a pharmaceutically acceptable carrier.

4. A method of treating tuberculosis, comprising administering a therapeutically effective amount of the pharmaceutical composition of claim 3 to a subject in need thereof.

5. The method of claim 4, wherein the tuberculosis comprises multiple drug resistance strains of *Mycobacterium tuberculosis*.

6. The method of claim 4, wherein the tuberculosis comprises H37Rv strains of *Mycobacterium tuberculosis*.

7. A method of treating tuberculosis, comprising administering a therapeutically effective amount of a pharmaceutical composition comprising a compound for treating tuberculosis and a pharmaceutically acceptable carrier, the compound having the following structural formula:

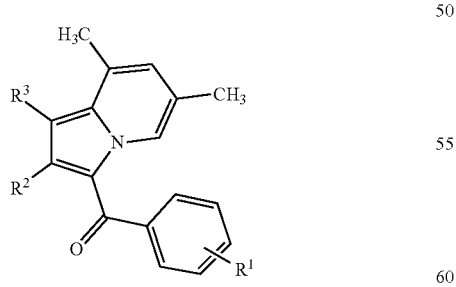

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

8. The method of claim 7, wherein the compound is selected from the group consisting of:

-continued

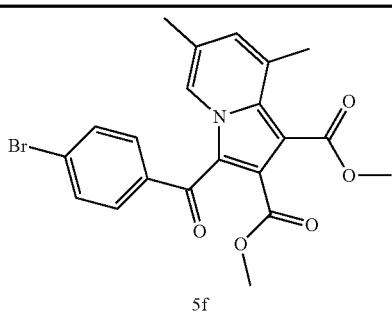

5f

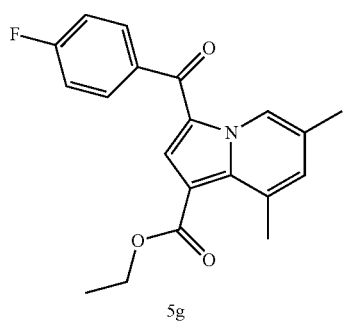

5g

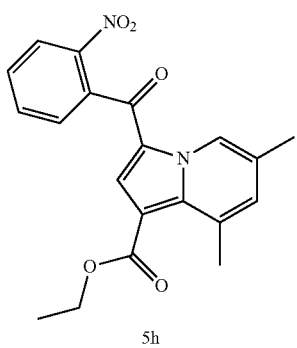

5h

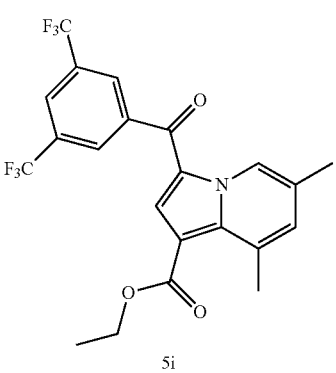

5i

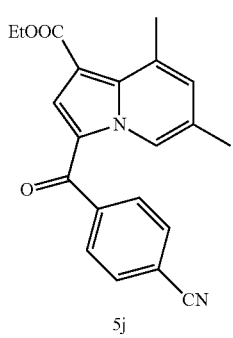

5j

-continued

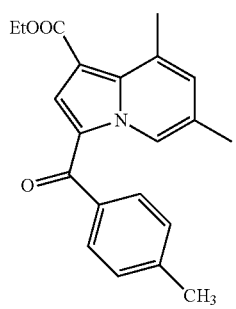 [SMILES: CCOC(=O)c1cc(C(=O)c2ccc(C)cc2)n2cc(C)cc(C)c12]

5k

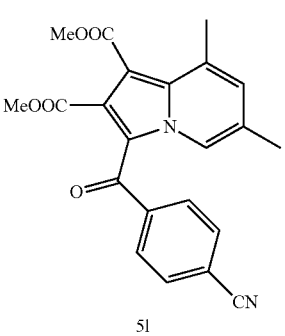

5l

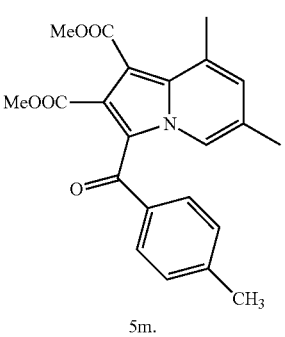

5m.

9. The method of claim 7, wherein the tuberculosis comprises multiple drug resistance strains of *Mycobacterium tuberculosis*.

10. The method of claim 7, wherein the tuberculosis comprises H37Rv strains of *Mycobacterium tuberculosis*.

11. A method of treating tuberculosis, comprising the step of administering to a patient in need thereof an effective amount of a compound having the formula:

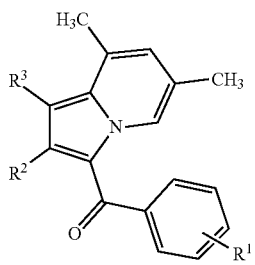

wherein $R^1$ is selected from the group consisting of 4-OCH$_3$, 4-Cl, 4-Br, 4-F, 2-NO$_2$, 3,5-CF$_3$, CN, CH$_3$, $R^2$ is COOCH$_3$, COOC$_2$H$_5$, and $R^3$ is H and COOCH$_3$.

* * * * *